United States Patent
Worth (10) Patent No.: US 10,816,522 B2
(45) Date of Patent: Oct. 27, 2020

(54) CONTINUOUS GAS DETECTION AND MONITORING APPARATUS FOR HARSH ENVIRONMENTS

(71) Applicant: Brian Worth, Woody Point (AU)

(72) Inventor: Brian Worth, Woody Point (AU)

(73) Assignee: Acrulog Pty. Ltd., Clontarf Qld (AU)

( * ) Notice: Subject to any disclaimer, the term of this patent is extended or adjusted under 35 U.S.C. 154(b) by 232 days.

(21) Appl. No.: 16/020,770

(22) Filed: Jun. 27, 2018

(65) Prior Publication Data
US 2019/0011416 A1    Jan. 10, 2019

(30) Foreign Application Priority Data

Jul. 7, 2017   (AU) ................................ 2017902658

(51) Int. Cl.
*G01N 33/00* (2006.01)
*G01N 11/04* (2006.01)

(52) U.S. Cl.
CPC ......... *G01N 33/0032* (2013.01); *G01N 11/04* (2013.01); *G01N 33/0006* (2013.01); *G01N 33/0063* (2013.01); *G01N 2033/0068* (2013.01)

(58) Field of Classification Search
CPC ........... G01N 33/0032; G01N 33/0006; G01N 33/0063; G01N 33/0009; G01N 33/0018; G01N 11/04
USPC ....................................................... 73/23.21
See application file for complete search history.

(56) References Cited

U.S. PATENT DOCUMENTS

| | | | | |
|---|---|---|---|---|
| 5,109,708 A | * | 5/1992 | Lawless | G01N 1/2258 73/28.01 |
| 5,473,951 A | * | 12/1995 | Tomlin | G01N 1/2247 73/863.83 |
| 6,085,576 A | * | 7/2000 | Sunshine | G01N 33/0031 73/29.01 |
| 6,198,400 B1 | * | 3/2001 | Church | G01N 33/0006 340/632 |
| 2017/0234845 A1 | * | 8/2017 | Worth | G01N 33/007 73/23.21 |

OTHER PUBLICATIONS

"Acrulog IPX H2S Dilution Monitor", Acrulog. (acrulog.com/products-rentals/h2s/ipx-ppm-dlu) accessed Apr. 8, 2020.*

* cited by examiner

*Primary Examiner* — Nimeshkumar D Patel
*Assistant Examiner* — Jean F Morello
(74) *Attorney, Agent, or Firm* — Michael W. Goltry; Robert A. Parsons; Parsons & Goltry, PLLC (57) ABSTRACT

A continuous gas detection and monitoring apparatus includes a gas detection and monitoring unit mounted in a sealable case, and a gas sensor in sealed fluid communication with an ambient atmosphere outside the case, a temperature and humidity sensor in sealed fluid communication with the inner volume of the case, a pressure sensor, data storage, and a gas sensor operatively connected to a data processor, and an externally operable switch for selectively connecting the data processor to the data storage to allow data transfer from the data storage to the data processor. A plumbing system includes a pump system, a solenoid system, and tubes interconnecting the gas sensor, pumping system, solenoid system, and ambient external environment. The gas sensor is mounted to the gas sensor housing and is in sealed fluid communication with the external environment via the plumbing system.

16 Claims, 8 Drawing Sheets

CONTINUOUS GAS DETECTION AND MONITORING APPARATUS FOR HARSH ENVIRONMENTS

CROSS-REFERENCE TO RELATED APPLICATION

This application claims the benefit of Australian Provisional Patent Application No. 2017902658, filed Jul. 7, 2017, the entire contents of which are incorporated herein by reference.

FIELD OF THE INVENTION

The present invention relates to an apparatus and methods for detecting and monitoring gases in chosen environments, such as wastewater infrastructures and other hostile environments.

BACKGROUND OF THE INVENTION

Gas detectors for detecting and/or monitoring harmful and/or offensive gases are widely used in industry, such as in industrial plants, refineries, pharmaceutical manufacturing facilities, fumigation facilities, paper pulp mills, aircraft and ship building facilities, hazmat operations, waste-water treatment facilities, and other hostile environments. Prior art gas detectors are inherently restricted in their capabilities and effective life in harsh or hostile environments due to the poor conditions and/or levels of corrosive substances and/or humidity. Moreover, sensor overload, sensor leakages, sensor drop off, and data loss due to excessive humidity uptake commonly occur in prior art gas sensors designed for use in hostile, humid environments. Given these and other deficiencies, the need for continued improvement in the art is evident.

SUMMARY OF THE INVENTION

A continuous gas detection and monitoring apparatus includes a gas detection and monitoring unit mounted in a sealable case. The case has at least a portion of it which is transparent allowing for viewing of the unit. The case is sealable to prevent ingress of the external environment into the inner volume. The continuous gas detection and monitoring unit includes a gas sensor in sealed fluid communication with an ambient atmosphere outside the case via a plumbing system, a temperature and humidity sensor in sealed fluid communication with the inner volume of the case, a pressure sensor, a data processor operatively connected to the gas sensor, the temperature and humidity sensor, and the pressure sensor, data storage and an information display operatively connected to the data processor, an externally operable switch for selectively connecting the data processor to the data storage to allow transfer of data from the data storage to the data processor, a communication device operatively connected to at least one of the data processor and the data storage for enabling data transfer between an external destination and at least one of the data processor and the data storage, a plumbing system incorporating, a pump system, a solenoid system, a series of tubes interconnecting the gas sensor, pumping system, solenoid system, and ambient external environment, so they are in sealable fluid communication with one another. A power supply mounted in the case and/or external power connector is operatively connected to power the continuous gas detecting and monitoring unit and provide signal output. The gas sensor is mounted to the gas sensor housing and is in sealed fluid communication with the external environment via the plumbing system. The temperature and humidity sensor is mounted to a PCB (printed circuit board) and is in fluid communication with the inner volume. The information display confronts one side of the case. The side confronted by the information display is preferably transparent to enable the viewing of the information display there through. The communication device is preferably a wireless communication device for enabling wireless data transfer between the external destination and at least one of the data processor and the data storage. The continuous gas detecting and monitoring unit further includes an inertial sensor sealed from the ambient atmosphere, and the data processor is operatively connected to the inertial sensor. The data processor is for calculating at least one of, and preferably both, moisture uptake level and moisture uptake rate of the inner volume, when the temperature and humidity sensor is sensing moisture of the inner volume inside the case.

According to the principle of the invention, a continuous gas detection and monitoring apparatus includes gas detection and monitoring unit mounted in a sealable portable case, a continuous gas detection and monitoring unit mounted in the case, the continuous gas detection and monitoring unit includes a gas sensor in sealed fluid communication with an ambient atmosphere outside the case, a temperature and humidity sensor in sealed fluid communication with the external environment of the case, an internal temperature and humidity sensor in fluid communication with the internal environment of the case, a humidity equalizer and/or control pack within the case, a pressure sensor in sealed fluid communication with the plumbing system, a data processor operatively connected to the gas sensor, the temperature and humidity sensor, and the pressure sensor, data storage and an information display operatively connected to the data processor, an externally operable switch for selectively connecting the data processor to the data storage to allow transfer of data from the data storage to the data processor, a communication device operatively connected to at least one of the data processor and the data storage for enabling data transfer between an external destination and at least one of the data processors and the data storage, a plumbing system including a pump system, a solenoid system, a series of tubes interconnecting the gas sensor, pumping system, solenoid system, differential pressure sensor, and ambient environments, and a power supply mounted in the case and/or external power connector is operatively connected to power the continuous gas detecting and monitoring unit. The gas sensor is mounted in the sensor housing and is in sealed fluid communication via a plumbing system. The inner temperature and humidity sensor is mounted to the unit and is in fluid communication with the internal environment of the apparatus. The temperature and humidity sensor is mounted to the unit and is in sealed fluid communication with the external environment of the apparatus via the plumbing system. The data process is for calculating at least one of moisture uptake level and moisture uptake rate of the internal environment, when either or both of the temperature and humidity sensors are sensing moisture of either the internal or external environments of the case. The apparatus is portable. The unit incorporates; a pump system, a solenoid system, a series of tubes, differential pressure sensor, and a gas sensor, which are in sealed fluid communication with each other and the external environments. A solenoid and/or pump system allows for alterable flow of material passing through the pipe system. The apparatus allows for dilution of fluid and/or gas passing through the pipe system. The pump system allows for a sample of the environment to be tested to be drawn from an extended range beyond the location of the continuous detection and monitoring apparatus. The unit alternates the flow of fluid and/or gas passing through the plumbing system, and revitalizes the sensor by exposure to a non-reactive environment. The unit alternates the flow of material passing through the plumbing system, and draw a fresh sample of the environment to flush the sensor prior to exposure to the gas sensor. The information display confronts one of the sidewalls of the case, and the section of the sidewall is transparent to enable the viewing of the information display therethrough. The apparatus includes a two way humidity control pack, to stabilize or adjust the internal humidity level of the apparatus. The communication device is a wireless communication device for enabling data transfer between the external destination and at least one of the data processor and the data storage, through either a direct connection, and/or a wireless connection. The gas detecting and monitoring unit further includes an inertial sensor sealed from the ambient atmosphere, and the data processor is operatively connected to the inertial sensor. The apparatus can accurately measure levels of gas beyond the normal recommended gas sensor capability. The apparatus can overcome issues experienced by electrochemical sensors when sampling in low oxygen environments. The apparatus allows for dilution of gas and/or fluids to be sampled with other gases and/or fluids. The apparatus dilutes the sample with an inert gas. The gas sample is diluted reducing level of exposure to the gas sensor, and/or the gas sensor is revitalized with exposure to a non-reactive environment. The pressure sensor is mounted to the unit and is in sealed fluid communication with the plumbing system. The pressure sensor detects the pressure within the plumbing system. The device is powered by either an external power supply, and/or a self-contained power supply. The device is calibrated to a specific target range through dilution of the known calibration sample.

BRIEF DESCRIPTION OF THE DRAWINGS

Referring to the drawings.

DETAILED DESCRIPTION

Figure 1:
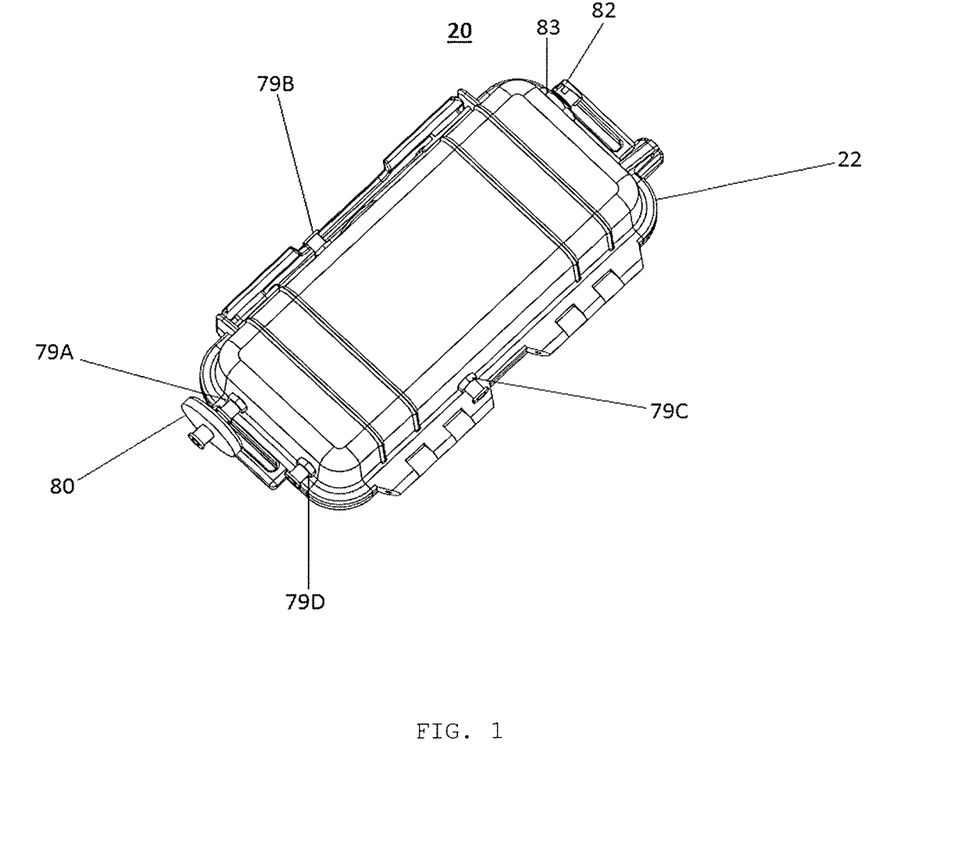
FIG. 1 is a front angled perspective view of the continuous gas monitoring apparatus constructed and arranged in accordance with the principle of the invention. The apparatus having a sealable case in which the device may be housed.
Figure 2:
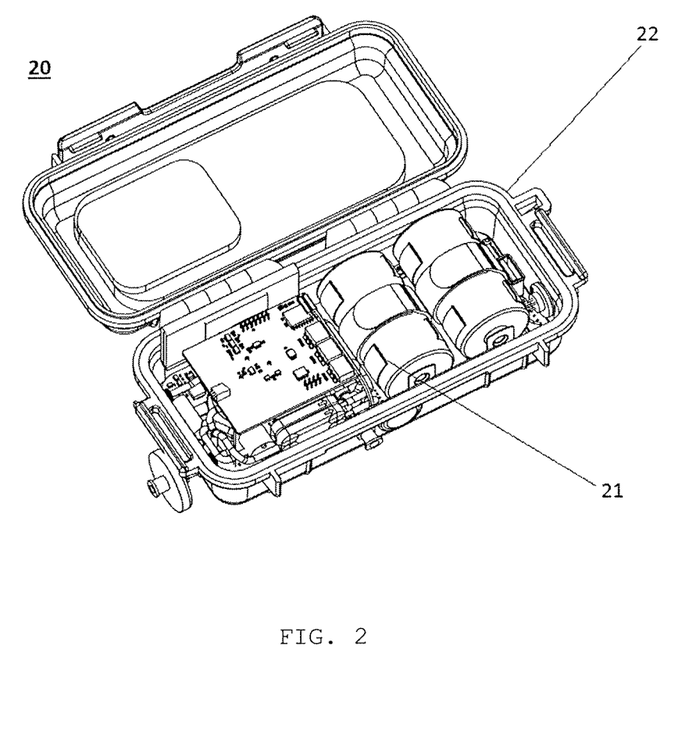
FIG. 2 is an open view of the apparatus with the device having been assembled and inserted into the casing in accordance with the principle of the invention.
Figure 3:
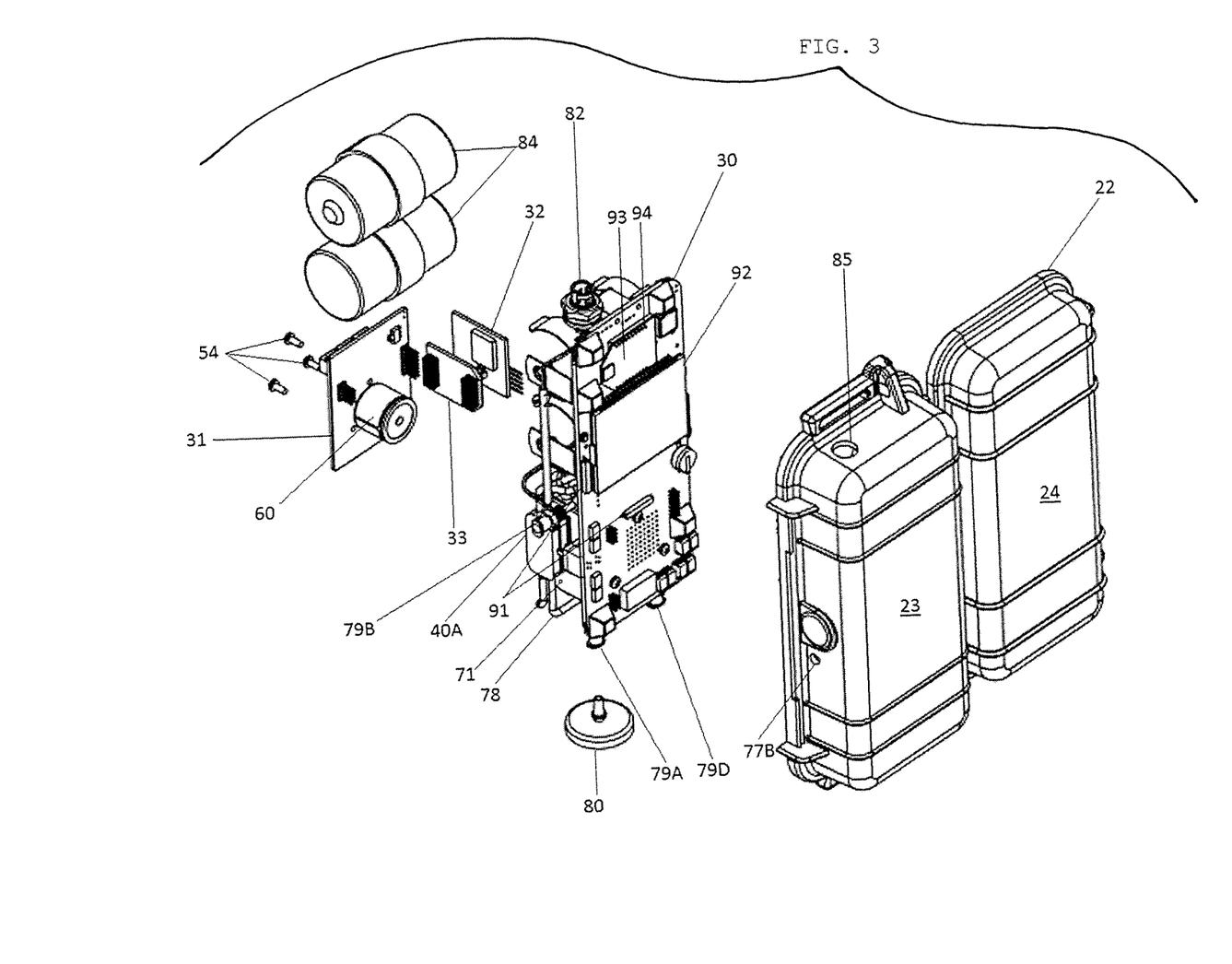
FIG. 3 is a front assembly view showing an exploded perspective of the continuous gas monitoring apparatus.
Figure 4:
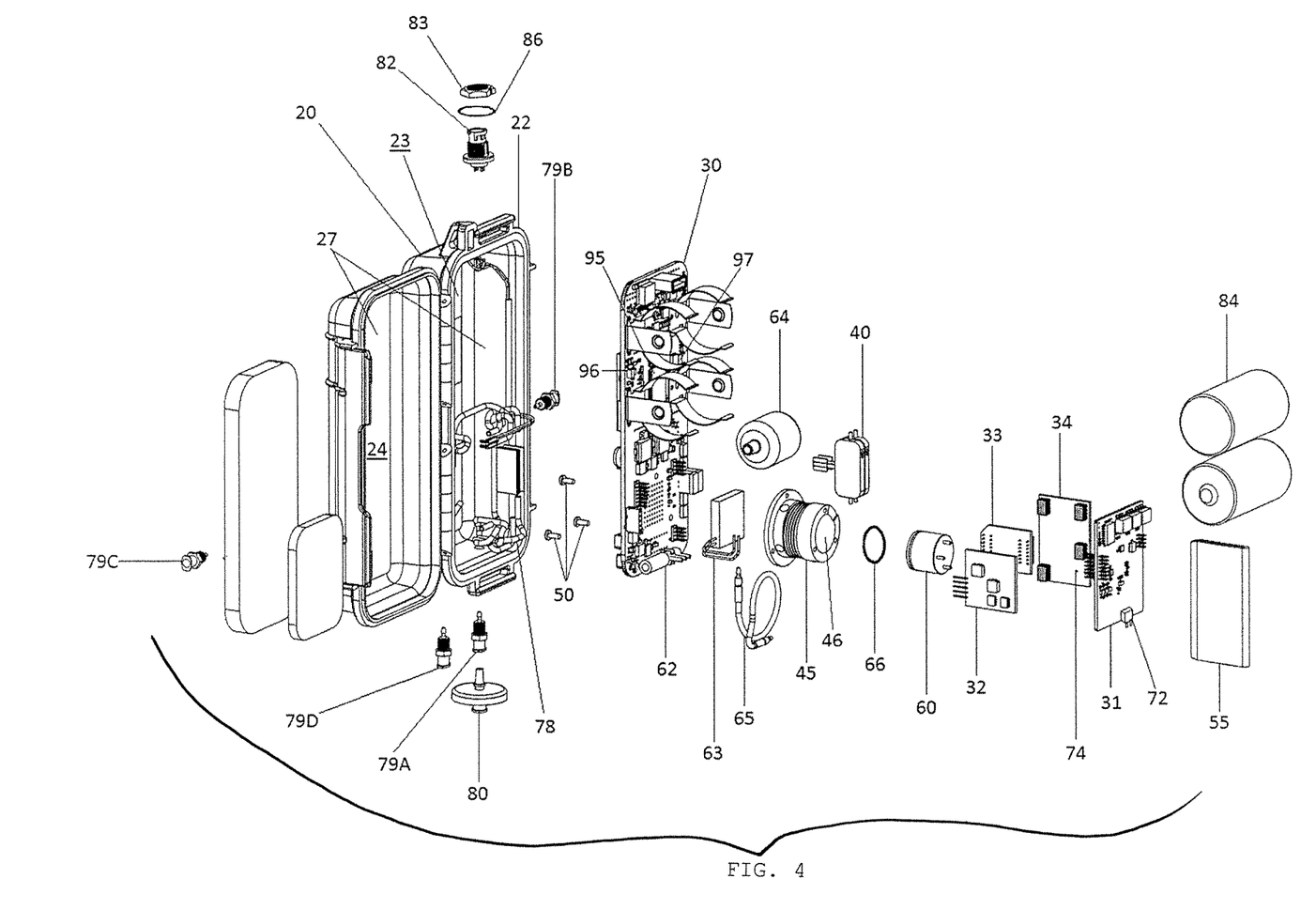
FIG. 4 is a rear assembly view showing an exploded perspective of the continuous gas monitoring apparatus.
Figure 5:
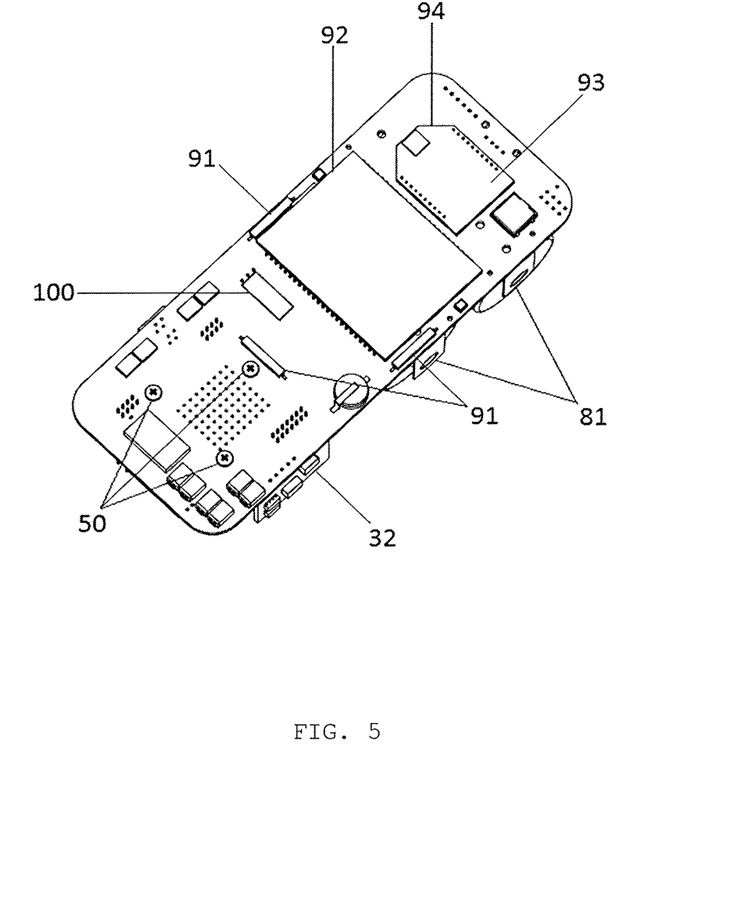
FIG. 5 is a front perspective of the unit assembled without the case.
Figure 6:
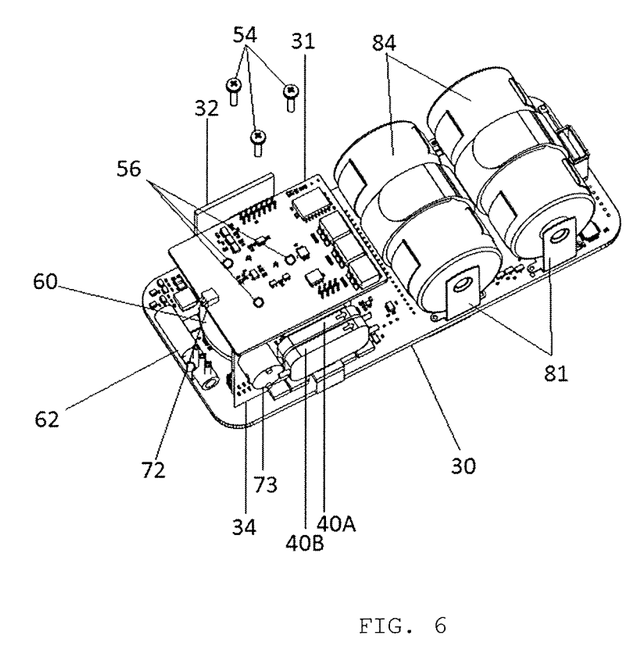
FIG. 6 is a rear perspective of the unit assembled without the case.
Figure 7:
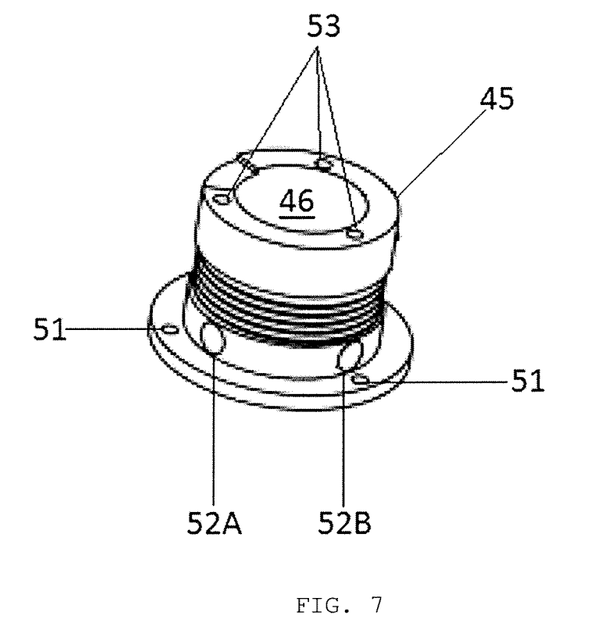
FIG. 7 is an angled top down perspective of the sensor housing.

Turning now to the drawings, in which like reference characters indicate corresponding elements throughout the several views, attention is directed to FIGS. 1-3 illustrating a continuous gas monitoring apparatus 20 including a case 22, and gas detection and/or monitoring apparatus 21, mounted in case 22. Front wall 23 is preferably a transparent material or a portion of front wall 23 is transparent to enable the contents of inner volume 27 to be viewed there through for unit 21 inspection and for visually identifying therein moisture and other unwanted contaminants.

Unit 21 is sealed in volume 27 of case 22 includes a variety of sensors, including gas sensor 60, temperature and humidity sensor 71, inner temperature and humidity sensor 74, and differential pressure sensor 72. Gas sensor 60 is sealed in recess 46 in sensor housing 45, and is in sealed fluid communication with an ambient environment outside case 22 via pipe system 78. Temperature and humidity sensor 71, and inner temperature and humidity sensor 74, are located on the temperature and humidity sensor board 34. Inner temperature humidity sensor 74 is in fluid communication with the internal environment of volume 27 within case 22. Temperature humidity sensor 71 is in sealed fluid communication with the external environment via the pipe system 78. Pressure sensor 72 is located on the Sensor PCB 31 and is in fluid contact with the pipe system 78 and detects/monitors differential pressure of the pipe system 78.

Figure 8:
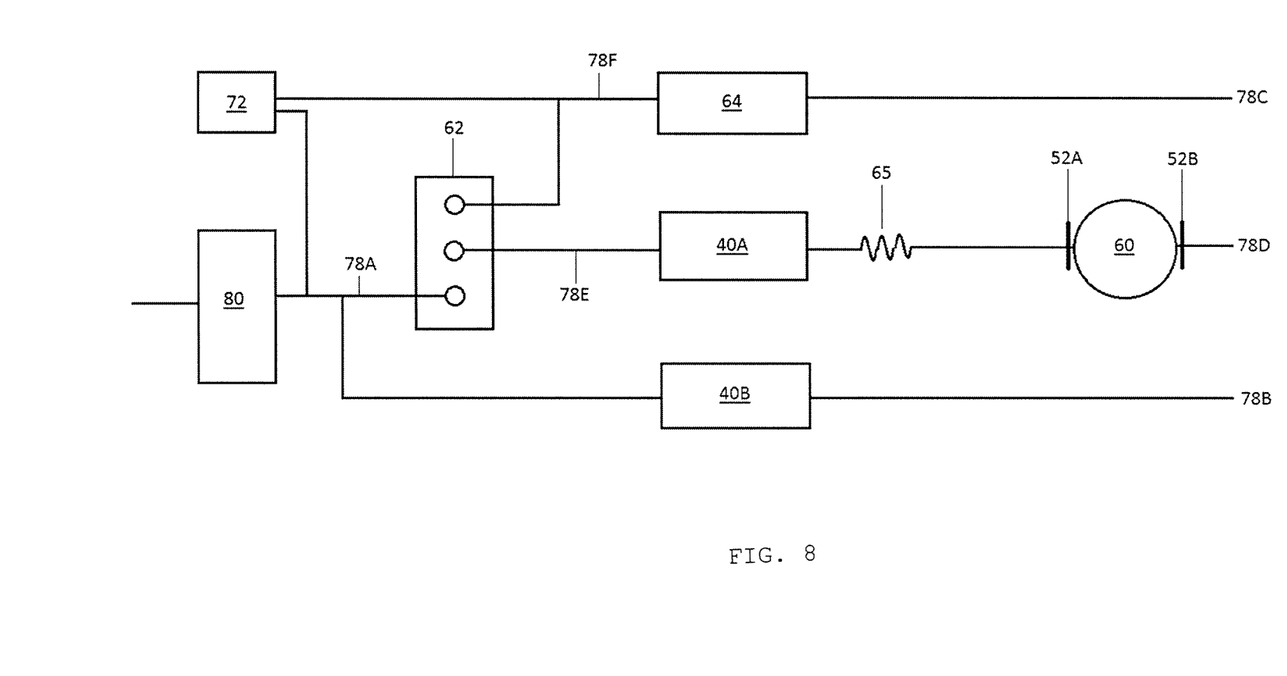
FIG. 8 is a representation of the plumbing system for the continuous gas monitoring apparatus.

The plumbing system of unit 21 is formed by a pipe system 78 comprising pipes 78A, 78B, 78C, 78D 78E and 78F which are in fluid communication with the external environment, an external filter 80, a solenoid 62, filter 64, pumps 40A and 40B two identical pumps, a non-gas permeable membrane tube 65, Peltier 63, gas sensor housing 45, gas sensor 60, and differential pressure sensor 72. Pipe 78A connects to an external filter 80 which is in turn connected to environmental flow port 79A at one end, the other end of pipe 78A connects to a Y connector which connects to solenoid 62 and pump 40B. Pump 40B connects to pipe 78B. Filter 80 is a filter that prevents the ingress of unwanted material into pipe 78A. Solenoid 62 is in fluid connection to the whole pipe system 78 and acts to alternate and control the flow of material exposed to non-gas permeable membrane tube 65 and subsequent parts, from pipes 78A, 78B, 78C and 78E. Pipe 78C connects to environmental flow port 79C at one end which is in fluid contact with an environment wherein the gas to be detected or monitored by continuous gas detection and monitoring apparatus 20 is preferably not present. Pipe 78C inter-connects to a filter 64 wherein unwanted matter can be filtered out prior to further continuance along pipe 78F. The other end of pipe 78F connects to solenoid 62. Non-gas permeable membrane tube 65, a filter, used to balance humidity to the inner volume 27, prior to gas exposure into recess 46 while at the same time enabling gas ingress to gas sensor 60 in recess 46, is connected to gas sensor housing environmental flow hole 52A at one end, the other end being connected to pump 40A at the other, and encircles gas sensor housing 45. Gas sensor 60 is sealed into recess 46 by gasket 66, preventing gas and moisture ingress into volume 27 of apparatus 20. Peltier 63 is in direct base contact with gas sensor housing and acts to stabilize temperature of the gas sensor housing 45 and subsequent gas sensor 60. Pipe 78D is connected to sensor housing environmental flow hole 52B and environmental flow port 79D which is in fluid connection with the external environment. Pipe 78D acts to release gas that has been exposed to gas sensor 60. Pipe 78B connects to environmental flow port 79B which is in fluid connection to the external environment. 79A connects to a Y connector which connects to solenoid 62 and pipe 78A.

Unit 21 incorporates a printed circuit board ("PCB") assembly, including main PCB 30, sensor PCB 31, Peltier PCB 32, connector PCB 33 and temperature and humidity PCB 34, which all carry, and electrically connects, the various components of unit 21. Main PCB 30 carries, and is electrically connected, to touch switch 100, three externally operable reed switches 91 act as secondary controls. Information display 92, a liquid crystal display ("LCD") in this example, that confronts, and that is visible through, front sidewall 23, communication device 93 and universal communication socket 94, data processor 95, inertial sensor 96, and data storage device 97. Battery mounts 81 connected to the back side of Main PCB 30 holds two batteries 84, dry cell battery packs in this example, that powers unit 21. When battery 84 is depleted, it may be removed from battery mounts 81 and replaced with fresh batteries. Apparatus 20, may also include external header 82. External header 82 is located towards the top of main PCB 30, above battery mounts 81, and is external to case 22 via external port hole 85. External header 82 is sealed in place by external header lock 83 and external header O-ring 86, forming a seal between external header lock 83 and case 22, to prevent the ingress of moisture, and other contaminants, into inner volume 27. External header 82 is operatively connected to apparatus 20 and may allow for external inputs to apparatus 20 and/or external power connection to apparatus 20. External header 82 may allow for a physical communication connection to one or more external locations. External Header 82 is operatively connected to at least one of data processor 95 and data storage device 97, and preferably both, for enabling data transfer between an external destination and at least one of data processor 95 and data storage device 97. Peltier PCB 32, connector PCB 33 and temperature and humidity PCB 34, connect adjacently to the main PCB 30 by a series of headers and connector pins and continue to form the circuits of unit 21, Sensor PCB 31 connects to, connector PCB 33 and temperature and humidity sensor PCB 34 to complete the series of circuits for unit 21. Gas sensor 60 is connected to sensor PCB 31. Sensor PCB 31 is fastened to sensor housing 45 by sensor housing fastening screws 54, being threaded through sensor board fastening holes 56 and sensor housing fastening holes 53. Peltier 63 is connected to Peltier PCB 32, temperature and humidity sensor 71, and inner temperature and humidity sensor 74, are connected to temperature and humidity PCB 34, pressure sensor 72 is carried by sensor PCB 31, and are all electrically connected to each other. Sensor PCB 31 is electrically connected to connector PCB 33 and Temperature and humidity PCB 34 and which are in turn connected to main PCB 30, Peltier PCB 32 connects to main PCB 30. main PCB 30 operatively connects data processor 95 to gas sensor 60, temperature and humidity sensor 71, inner temperature and humidity sensor 74, pressure sensor 72, inertial sensor 96, data storage device 97, display 92, and Peltier 63, all of which work in concert with one another.

Calibration of unit 21 operatively connects gas sensor 60 to data processor 95 for calibrating data processor 95 to a predetermined gas concentration measured by gas sensor 60 from exposure to an accurately pre-measured and known source, when data processor 95 has been configured to predetermine settings prior to calibration of unit 21. Touch switch 100 is externally operable for selectively connecting data processor 95 to data storage device 97 to allow transfer of data from data storage device 97 to data processor 95. Communication device 93 is operatively connected to at least one of data processor 95 and data storage device 97, and preferably both, for enabling data transfer between an external destination and at least one of data processor 95 and data storage device 97. Communication device 93 is a conventional wireless communication device for enabling wireless data transfer between the external destination and at least one of data processor 95 and data storage 97. Communication device 93 may employ one or more wireless communication protocols, such as radio frequency, Wi-Fi, and/or one or more other chosen wireless communication protocols. Inertial sensor 96 is sealed in volume 27 from the ambient atmosphere. Inner temperature and humidity sensor 74, operates as a moisture level indicator, in volume 27 of case 22, is for showing, via display 92, a moisture reading in volume 27 of case 21 determined by data processor. Apparatus 20 can be repaired or serviced, when visual display 92 displays a predetermined level pre-programmed into processor 95, indicating moisture in volume 27, by opening case 22 withdrawing unit 21 from volume 27 to enable the skilled worker to carry out necessary repairs and/or maintenance.

Apparatus 20 is portable, in that it is easily taken up by hand and carried about for installation in a selected environment. Apparatus 20 is installed in an environment in which a particular gas is to be detected and monitored by securing apparatus 20 to selected location by suspending or supporting apparatus 20 in the chosen environment from case 22. Apparatus 20 is switched on exteriorly, and operated exteriorly by, touch switch 100 and operates according to instructions pre-programmed into data processor 95, and operates within the ambient environment without the use of external controls. Touch switch 100 is conventional, is enclosed in volume 27 adjacent to side wall 23, and is operated exteriorly by touching the outer surface of sidewall 23 opposite to touch switch 100, requiring no physical contact with touch switch 100. The reed switches 91 of unit 21 are similarly exteriorly operable. Gas sensor 70, temperature and humidity sensor 71, inner temperature and humidity sensor 74, are in contact with their respective environments concurrently detect and monitor, in real time, gas, and temperature and humidity uptake. Real time monitoring of humidity level via temperature and humidity sensor 71, and/or inner temperature humidity sensor 74, prevents gas sensor 60 leakage when data processor 95 calculates humidity uptake of gas sensor 60. Inertial sensor 96, in turn, and concurrently with the other sensors, senses, in real time, accelerations and movements that can occur if apparatus 20 is moved. Data processor 95 operatively coupled to the various sensors records and stores the data from the various sensors in data storage device 97, and displays the data on display 92 viewable through sidewall 23. Display 92 is large, enabling it to display all of the sensor data and calculations made by data processor 95. Communication device 93 operatively connected to at least one of data processor 95 and data storage device 97, and preferably both, enables transfer of the data between an external destination and at least one of data processor 95 and data storage device 97. Communication device 93 is preferably a conventional wireless communication device in a preferred embodiment for enabling wireless data transfer between the external destination and at least one of data processor 95 and data storage 97. Unit 21 can incorporate an alarm, such as an audible and/or visual alarm, operatively connected to data processor 95 and set to issue an audible and/or visual alarm when a concentration of gas being measured by gas sensor 60 reaches a predetermined level, when unit 21 is calibrated, and when unit 21 is set to predetermined settings. In a particular embodiment, data processor 95 transmits a signal wirelessly to an external destination when a concentration of gas being measured by gas sensor 60 reaches a predetermined level to alert a skilled worker that the concentration of gas being measured has reached a predetermined level.

Unit 21 allows for alterable fluid communication between pipes 78A, 78B, 78C, 78D, 78E and 78F and their respective connections thereon, via the solenoid 62 and pumps 40A and 40B. Alternations can be programed to occur by data processor 95 communicating with solenoid 62 or pumps 40A and 40B to perform certain actions when data processor 95 achieves a certain condition that is programmed into data processor 95.

Apparatus 20 can dilute and/or mix gas and/or fluids. As previously mentioned above, the device 21 can alternate the flow of material passing through the plumbing system. Solenoid 62 may alternate the flow of material passing through pipes 78F and 78A to 78E and subsequent parts. Solenoid 62 alternates when it receives a signal from data processor 95 to perform a specified action. Pumps 40A and 40B further allow for the manipulation and alternating of fluid and/or gas passing through the plumbing system. Pumps 40A and 40B are connected to data processor 95 and may be sent a signal by processor 95 to be switched on or off upon a programmed goal having been met by data processor 95. Solenoid 62, pumps 40A and 40B working in conjunction with each other by the direction of data processor 95, and allows for dilution to a pre-programmed ratio of fluid and/or gas entering the plumbing system. As a result of apparatus 20 being able to dilute fluid and/or gas prior to exposure to the sensor 60, the unit 21 may be more accurately calibrated to detect and monitor lower level fluids or gases when calibrated from a standard gas calibration bottle at the target range required.

As described above, gas sensor 60, and temperature and humidity sensor 71 are in fluid contact with the ambient environment outside case 22, inner temperature and humidity sensor 74 in fluid contact with inner volume 27, concurrently detect and monitor, in real time, gas, temperature, humidity, and pressure, respectively, of their environments. During operation of unit 21, data processor 95 calculates the moisture, i.e. humidity, uptake level and moisture uptake rate of the gas sensor 60, and displays the calculated moisture uptake level and rate on display 92 in response enabling the skilled worker to extrapolate how long to deploy apparatus 20 at the chosen environment, when either temperature and humidity sensor 71 or inner temperature and humidity sensor 74, are sensing moisture, i.e., humidity/moisture uptake level and humidity/moisture uptake rate, of the inner volume 27 of case 22. Furthermore, the calculated uptake level of gas sensor 60 enables the skilled worker to extrapolate the length of time needed to dry out the gas sensor 60 in a chosen controlled environment before apparatus 20 can be re-deployed. Unit 21 can incorporate an alarm, such as an audible and/or visual alarm, operatively connected to data processor 95 and set to issue an audible and/or visual alarm when the moisture uptake level measured by inner temperature and humidity sensor 74 reaches a predetermined level, and/or when the moisture uptake rate measured by inner temperature and humidity sensor 74 reaches a predetermined rate, to enable the skilled worker to remove apparatus 20 from the chosen environment for drying out and for preventing gas sensor 60 from filling up and leaking in real time. In a particular embodiment, data processor 95 transmits a signal wirelessly to an external destination when the moisture uptake level measured by inner temperature and humidity sensor 74 reaches a predetermined level, and/or when the moisture uptake rate measured by inner temperature and humidity sensor 74 reaches a predetermined rate, to enable the skilled worker to remove apparatus 20 from the chosen environment for drying out gas sensor 60 and for preventing the gas sensor 60 from filling up and leaking in real time. Alternatively, as previously described above, the device 21 can alternate the flow of fluids and/or gases prior to exposure to gas sensor 60 and may be programmed for data processor 95 to instruct solenoid 62 and pumps 40A and 40B to act in such a way as to expose the sensor 60 to non-reactive fluid and/or gas where the device is in sealed fluid communication via pipe 78C to a non-reactive environment, allowing sensor 60 to dry out. Humidity control pack 55, is a two-way humidity control, and may maintain the inner volume humidity to a predetermined level. Humidity control pack 55, is located between front case wall 23, rear case wall 24, and is in sealed fluid communication with the inner volume 27.

The present invention is described above with reference to illustrative embodiments. However, those skilled in the art will recognize that changes and modifications may be made in the described embodiments without departing from the nature and scope of the present invention. Various further changes and modifications to the embodiments herein chosen for purposes of illustration will readily occur to those skilled in the art. To the extent that such modifications and variations do not depart from the spirit of the invention, they are intended to be included within the scope thereof.

Having fully described the invention in such clear and concise terms as to enable those skilled in the art to understand and practice the same, the invention claimed is:

1. A continuous gas detection and monitoring apparatus, comprising;
    a gas detection and monitoring unit mounted in a sealable portable case, the continuous gas detection and monitoring unit includes;
    a gas sensor in sealed fluid communication with an external environment outside the case;
    a temperature and humidity sensor in sealed fluid communication with the external environment;
    an internal temperature and humidity sensor in fluid communication with an internal environment inside the case;
    a humidity equalizer and/or control pack within the case;
    a pressure sensor in sealed fluid communication with a plumbing system;
    a data processor operatively connected to the gas sensor, the temperature and humidity sensor, and the pressure sensor;
    data storage and an information display operatively connected to the data processor;
    an externally operable switch for selectively connecting the data processor to the data storage to allow transfer of data from the data storage to the data processor;
    a communication device operatively connected to at least one of the data processor and the data storage for enabling data transfer between an external destination and at least one of the data processors and the data storage;
    the plumbing system incorporating:
        a pump system, a solenoid system, a pipe system interconnecting the gas sensor, the pump system, the solenoid system, the pressure sensor, and the external environment, and
        a power supply mounted in the case and/or external power connector is operatively connected to power the continuous gas detecting and monitoring unit.

2. The continuous gas detection and monitoring apparatus according to claim 1, wherein the gas sensor is mounted in a sensor housing and is in sealed fluid communication with the external environment via the plumbing system.

3. The continuous gas detection and monitoring apparatus according to claim 1, wherein the internal temperature and humidity sensor is mounted to the unit and is in fluid communication with the internal environment.

4. The continuous gas detection and monitoring apparatus according to claim 1, wherein the temperature and humidity sensor is in sealed fluid communication with the external environment via the plumbing system.

5. The portable gas detecting and monitoring apparatus according to claim 1, wherein the data process is for calculating at least one of moisture uptake level and moisture uptake rate of the internal environment, when either or both of the temperature and humidity sensors are sensing moisture of either the internal environment or the external environments.

6. The continuous detection and monitoring apparatus according to claim 1, wherein the pump system, the solenoid system, the pipe system, the pressure sensor, and the gas sensor are in sealed fluid communication with each other and the external environment.

7. The continuous detection and monitoring apparatus according to claim 6, wherein the solenoid system and/or the pump system allows for alterable flow of material passing through the pipe system.

8. The continuous detection and monitoring apparatus according to claim 7, wherein the apparatus allows for dilution of fluid and/or gas passing through the pipe system.

9. The continuous gas detection and monitoring apparatus according to claim 8, wherein the apparatus allows for dilution of gas and/or fluids to be sampled with other gases and/or fluids.

10. The continuous gas detection and monitoring apparatus according to claim 9, wherein the apparatus dilutes the gas and/or fluids to be sampled with an inert gas.

11. The continuous gas detection and monitoring apparatus according to claim 1, wherein the information display confronts a section of a sidewall of the case, and the section of the sidewall is transparent to enable the viewing of the information display therethrough.

12. The continuous detection and monitoring apparatus according to claim 1, wherein the apparatus includes a two-way humidity control pack, to stabilize or adjust an internal humidity level of the apparatus.

13. The continuous gas detection and monitoring apparatus according to claim 1, wherein the communication device is a wireless communication device for enabling data transfer between the external destination and at least one of the data processor and the data storage, through either a direct connection, and/or a wireless connection.

14. The continuous gas detection and monitoring apparatus according to claim 1, wherein the gas detecting and monitoring unit further includes an inertial sensor sealed from the ambient atmosphere, and the data processor is operatively connected to the inertial sensor.

15. The continuous gas detection and monitoring apparatus according to claim 6, wherein the pressure sensor is mounted to the unit and is in sealed fluid communication with the plumbing system.

16. The continuous gas detection and monitoring apparatus according to claim 15, wherein the pressure sensor detects pressure within the plumbing system.

* * * * *